United States Patent
Donders et al.

[11] Patent Number: 6,115,634
[45] Date of Patent: Sep. 5, 2000

[54] IMPLANTABLE MEDICAL DEVICE AND METHOD OF MANUFACTURE

[75] Inventors: Adrianus P. Donders, Andover, Minn.; Terence G. Ryan, Palm Coast, Fla.; Keon J. Weijand, Hoensbroek, Netherlands; Craig Wiklund, Bloomington, Minn.

[73] Assignee: Medtronic, Inc., Minneapolis, Minn.

[21] Appl. No.: 08/841,709

[22] Filed: Apr. 30, 1997

[51] Int. Cl.⁷ .................................................. A61N 1/362
[52] U.S. Cl. .................................................................. 607/32
[58] Field of Search .................. 607/32, 30, 31, 607/9

[56] References Cited

U.S. PATENT DOCUMENTS

| | | | |
|---|---|---|---|
| 4,440,173 | 4/1984 | Hudziak et al. | 128/419 PG |
| 4,661,212 | 4/1987 | Ehrfeld et al. | 204/11 |
| 4,990,827 | 2/1991 | Ehrfeld et al. | 313/533 |
| 5,073,237 | 12/1991 | Bacher et al. | 264/320 |
| 5,150,183 | 9/1992 | Mikosch et al. | 357/32 |
| 5,166,826 | 11/1992 | Ruprecht | 359/566 |
| 5,190,637 | 3/1993 | Guckel | 205/118 |
| 5,234,571 | 8/1993 | Noeker | 205/70 |
| 5,260,175 | 11/1993 | Kowanz et al. | 430/326 |
| 5,298,367 | 3/1994 | Hoessel et al. | 430/326 |
| 5,311,604 | 5/1994 | Rogner et al. | 385/14 |
| 5,342,408 | 8/1994 | DeCoriolis et al. | 607/32 |
| 5,350,499 | 9/1994 | Shibaike et al. | 204/192.34 |
| 5,378,583 | 1/1995 | Guckel et al. | 430/325 |
| 5,562,714 | 10/1996 | Grevious | 607/32 |

FOREIGN PATENT DOCUMENTS

| | | |
|---|---|---|
| WO93/25732 | 12/1993 | Germany . |
| 0 618 502 A1 | 2/1994 | Germany . |
| 0 620 092 A1 | 2/1994 | Germany . |
| WO94/11719 | 5/1994 | Germany . |
| WO94/18605 | 8/1994 | Germany . |

OTHER PUBLICATIONS

Application of the LIGA technique for the development of microactuators based on electromagnetic principles—(J. Micromech. Microeng. 2 (1992) 229–233) H. Lehrt et al.
Trends In Micromechanics—Micron Machinations (Scientific America, Nov. 1992), G. Stix.
Micromachines on the March—(IEEE Spectrum May 1994), J. Bryzek et al.

*Primary Examiner*—Scott M. Getzow
*Attorney, Agent, or Firm*—Thomas F. Woods; Michael J. Jaro; Harold Patton

[57] ABSTRACT

An implantable medical device having a hermetic canister a battery positioned within the hermetic canister; a pulse generator system positioned within the hermetic canister and electrically coupled to the battery; a receiver positioned within the hermetic canister and electrically coupled to the battery and the pulse generator system; a transmitter positioned within the hermetic canister and electrically coupled to the battery and the pulse generator system; and an antenna positioned outside the hermetic canister and coupled to the pulse generator by a feedthrough. The antenna is constructed of a series of planar windings enclosed by an enclosure; each winding is between 1–100 microns wide, wherein each winding is between 1–1000 microns thick and wherein each winding is spaced apart from each of the other windings between 1–100 microns. In the preferred embodiment the antenna has a closely spaced concentric winding of a conductive material, preferably gold, the winding having 30 turns, wherein is conductive material 25 microns wide, 100 microns thick, and each winding is spaced apart from each of the other turns by 20 microns.

49 Claims, 15 Drawing Sheets

IMPLANTABLE MEDICAL DEVICE AND METHOD OF MANUFACTURE

FIELD OF THE INVENTION

This invention relates to implantable medical devices and, more particularly, to implantable medical devices featuring a biocompatible antenna and a method of manufacturing the same.

BACKGROUND OF THE INVENTION

For several decades, electronic devices have been implanted in humans and animals. Such devices are generally used to monitor or regulate the functions of body organs and the like. For example, a pacemaker monitors and regulates heart rate, delivering electrical impulses as required to maintain a satisfactory heart beat. Such implantable devices are powered by batteries which have a finite capacity, and which also present a limitation in terms of available peak power. As a result, there is a significant need to minimize the energy expended during operation of the implantable device, and to reduce the peak power required for special situations such as communications with external devices.

In recent years, implantable electronic device technology has rapidly advanced. Sizes and weights have decreased, while functionality has increased. These advances have created a corresponding demand for two-way communication or telemetry between the implanted electronic device and an external device, generally known as a programmer. In a pacemaker system, for example, a programmer downloads data to an implanted pacemaker, such as operating parameters. Likewise, data may flow in the opposite direction, that is from the implanted device to the programmer for analysis. In fact, modern pacemakers are capable of storing significant amounts of data about the patient (e.g., average heart rate) and the pacemaker (e.g. battery voltage) which may need to be frequently telemetered or transmitted to the programmer for evaluation by the physician.

Modern telemetry systems, however, are subject to competing requirements. They must transmit large amounts of data in a reasonable rapid manner. They must also transmit such data while using as little current from the battery as possible. Finally, they must meet these requirements while typically housed within a metallic hermetic canister.

Most modern implantable devices feature a metallic hermetic canister in order to withstand prolonged exposure to the harsh in vivo embodiment. Numerous factors, including human immune response, chemical reactivity, temperature, mechanical stresses, and the like, contribute to the harshness of this environment on implanted objects. As a result, every component of an implantable device must be biostable and biocompatible, or else surrounded or encased in a container or coating which is biostable and biocompatible.

A cardiac pacemaker, for example, typically features a hermetically sealed metallic housing, such as titanium. In particular, titanium has been found to be one of the few acceptable metals from which the hermetic canister may be made. Several other metals may also be acceptable, such as gold or platinum, but these are not commercially acceptable due to their cost. Other metals are generally unsuitable for implant in the body due to their tendency to corrode. Moreover, most other materials, such as many plastics and other synthetic materials, which appear to be suitably resistant to the environment in the short term, nonetheless permit seepage of body fluids over the long term.

One advantage of using a metal for the hermetic canister is that the canister itself is conductive. This conductivity may be exploited, for example, by utilizing the canister itself as an electrode.

The conductivity of the implanted device enclosure, however, also has at least two significant disadvantages in regards to the telemetry system. First, the metal enclosure attenuates the electromagnetic field strength of signals transmitted to and from the implantable device. During uplink or communication from the implanted device, this attenuation may be overcome by increasing the strength of the transmitted signal. This increased signal strength, however, increases the current drain on the battery thereby diminishing the device longevity. Thus, in most cases, it is necessary to place the external programming device as close as possible to be implantable medical device so the signal strength may be thus be kept as low as possible and the battery not unnecessarily depleted. Second, the metallic housing also has a limiting effect upon the rate at which data may be transmitted between the implantable device and the external program.

Of course, a device having its antenna disposed outside the metallic hermetic canister would not suffer from these drawbacks. Such an antenna, however, because it must be either biocompatible or encased within a biocompatible material and must as well as be of a suitable configuration and have suitable performance, has not been developed to date. Thus, there is a long-felt need for a more efficient telemetry system for use with implantable devices, and specifically for an improved antenna which is both biocompatible and biostable so that it may be positioned outside of the metallic hermetic canister.

SUMMARY OF THE INVENTION

It is thus an object of the present invention to provide an implantable medical device which has a biocompatible and biostable antenna.

It is a further object of the present invention to provide an implantable medical device which has an antenna which may be positioned outside of the hermetic canister.

It is a further object of the present invention to provide an implantable medical device which has an antenna which may be mounted within the connector block assembly of the device, outside of the hermetic canister of the device.

These and other objects are met by the present invention which provides an implantable medical device having a hermetic canister a battery positioned within the hermetic canister; a pulse generator system positioned within the hermetic canister and electrically coupled to the battery; a receiver positioned within the hermetic canister and electrically coupled to the battery and the pulse generator system; a transmitter positioned within the hermetic canister and electrically coupled to the battery and the pulse generator system; and a biocompatible antenna positioned outside the hermetic canister and coupled to the pulse generator by a feedthrough. The antenna is constructed of a series of planar windings enclosed by an enclosure; wherein each winding is between approximately 1–1000 microns thick and wherein each winding is spaced apart from each of the other windings between approximately 1–100 microns. In a preferred embodiment, the antenna has a closely spaced concentric winding of a conductive material, preferably gold, of 30 turns wherein the conductive material is approximately 25 microns wide, each winding being approximately 100 microns thick, and each winding being spaced apart from each of the other windings by approximately 20 microns.

BRIEF DESCRIPTION OF THE DRAWINGS

The foregoing summary, as well as the following detailed description of the preferred embodiment, is better understood when read in conjunction with the appended drawings. While the drawings illustrate preferred embodiments, it is to be understood that the invention is not limited to the specific methods and instrumentalities disclosed.

DETAILED DESCRIPTION OF THE PREFERRED EMBODIMENTS

Figure 1:
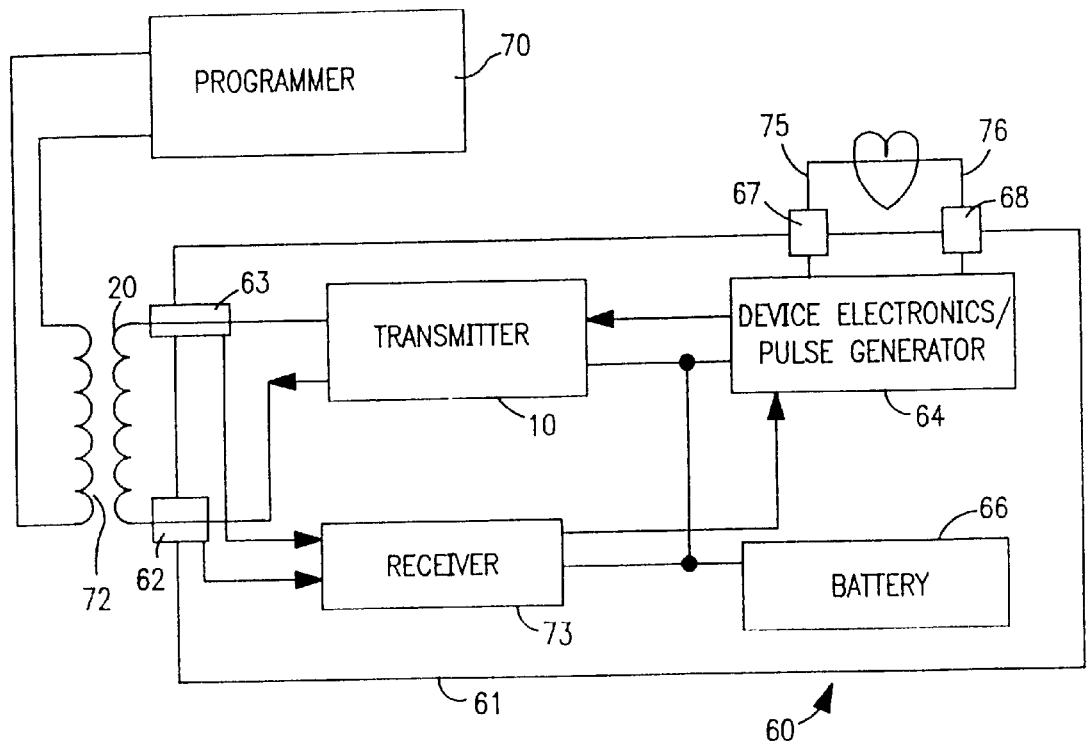
FIG. 1 is a block diagram of an implantable medical device in communication with an external device.

Referring to FIG. 1, a block diagram of an implantable device 60 in telemetric communication with an external device 70 (i.e., a programmer) is shown. In such a system, the programmer 70 downloads information to the implantable device 60, and the implantable device 60 up-links information to the programmer 70. The two devices 60 and 70 communicate via an inductive link provided by antenna coils 20 and 72. Thus when the programmer coil 72 is brought into proximity with the implantable device coil 20, a current flow through either antenna coil 20, 72 causes an inductive current in the other coil 72, 20.

In the illustrative system, device 60 is an implantable pacemaker, and programmer 70 is adapted in a known manner to be used by a physician to communicate with the pacemaker. Device 60 further features hermetic canister 61. Hermetic canister 61 has four feed through pins 62, 63, 67, 68 mounted therein. Two of the feed through pins 67, 68 are used to provide an electrical coupling to a pair of medical electrical leads 75, 76 which are coupled, in turn, to a patient's heart. The other two feed through 62, 63 pins couple the transmitter 10 and receiver 73 to the antenna 20, positioned outside the hermetic canister 61.

A typical up-link telemetry path begins with a request by the programmer 70 for information from the device 60. In such a case, the device 60 detects and demodulates the request from the programmer 70. The demodulated command then passes to the device electronics 64 as indicated by the arrows. The device electronics 64 retrieves the requested information from memory (not shown separately), and prepares the information for up-link, passing a digital data stream to transmitter 10. The transmitter 10 uses this digital data to appropriately modulate the current flow through coil 20, which current in turn induces a current in coil 72. The receiver 73 in the programmer 70 receives and demodulates the data transmitted from the device 60, completing the telemetry path. Data received in the programmer is processed by the device electronics. During transmission from programmer 70, device electronics controls the encoding of data for transmission from transmitter 170 to the device 60.

Implanted device 60 further has a power supply 66, suitably a battery, which provides the power for all of the implantable device circuitry and components. That is, the receiver 62, the device electronics 64 and the transmitter 10 all must share a single power supply 66. As a result, the more frequently the telemetry system is employed, or the less efficient the telemetry system is, the faster the power supply 66 will be depleted. Furthermore, although the system has two-way communication, the bulk of the information flows from the implantable device 60 to the programmer 70. Thus, an energy efficient transmitter 10 will enhance the lifespan of the implantable device 60. Further, with the power supply limitations of a typical implanted device, transmitter efficiency is important in order to provide a good rate of data transmission, which is very important for optimizing the attending doctor's time.

Figure 2A:
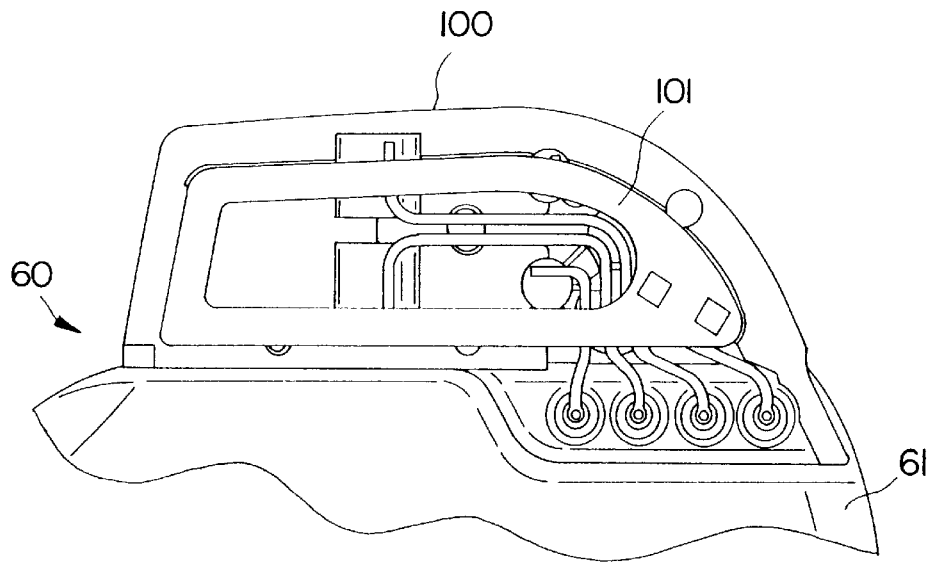
FIG. 2A is a view of an implantable medical device depicted in FIG. 1 and showing in particular an antenna according to the present invention mounted within the connector block assembly of an implantable medical device.

FIG. 2A is a view of an implantable medical device depicted in FIG. 1. As seen only a portion of the device showing the biocompatible antenna 101 mounted within connector block assembly 100 is shown. One important aspect, however, of the present invention may be seen in this view. As seen the biocompatible antenna is essentially a series of concentric planar windings about a first axis, the hermetic canister has a major plane, the first axis being perpendicular to the major plane. This relationship between the major plane of the device and the axis of the antenna means the most sensitive direction of the antenna is in a direction perpendicular to the major plane of the device. This is important because it means when the device is implanted, the antenna is most sensitive in a direction which is the closest distance to the patient's surface, i.e. in a direction in which an external device such as a programmer head may be positioned.

Figure 2B:
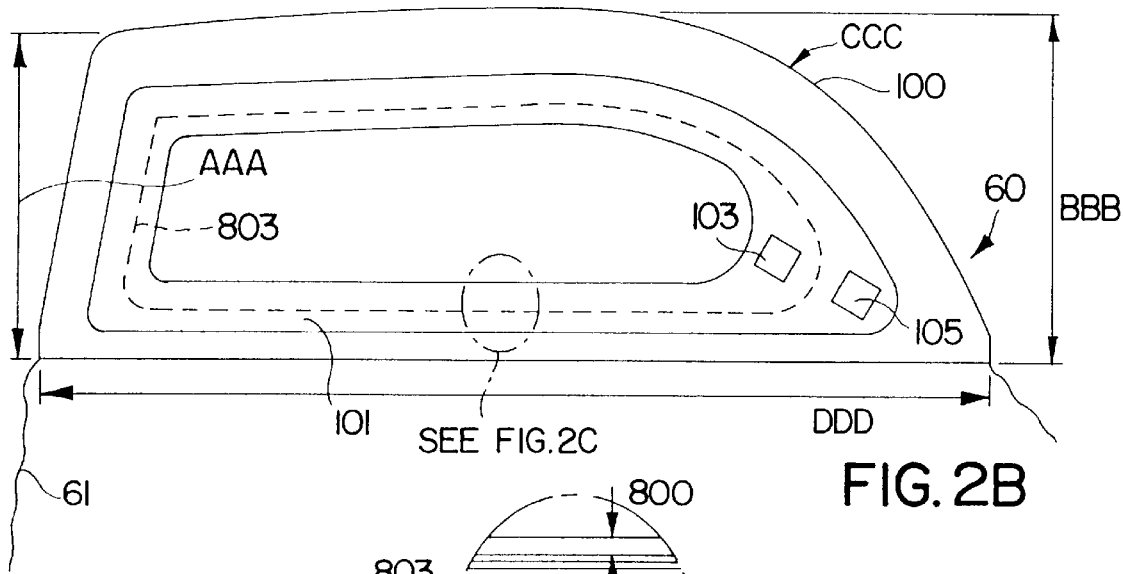
FIG. 2B depicts the relative size of the antenna compared to the connector block.
Figure 2C:
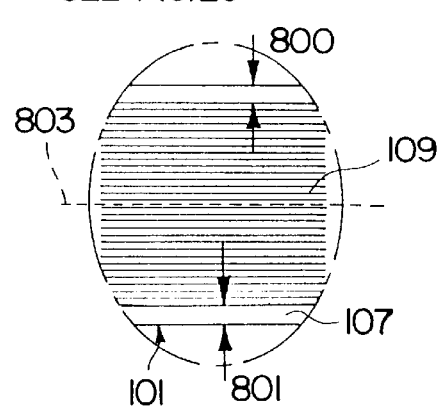
FIG. 2C is a detailed view of the antenna shown in FIG. 2B.

FIG. 2B depicts the relative size of the antenna 101 compared to the connector block 100. As seen connector block has the following dimensions: AAA is 0.465 inches; BBB is 0.500 inches, CCC is 0.574 in radius and DDD is 1.324 inches. As more fully discussed below, antenna 101 consists of a series of concentric windings 109 enclosed within a biocompatible enclosure 107. As best seen in FIG. 2C, because the enclosure extends 800 beyond the outermost winding and extends 801 beyond the innermost winding an equal amount, 0.009 inches in the preferred embodiment, the average aperture 803 of the windings used in the antenna may be determined by averaging the inner and outer surface areas of the antenna. As seen antenna (the term which as used here includes both the windings and the enclosure) has an outer surface area of 0.349 square inches and an inner surface area of 0.167 square inches. Thus the average surface area of the aperture of the windings used in the antenna is 0.258 square inches. As seen, the antenna is positioned within the connector block. In the preferred embodiment the projected surface area of the connector block (i.e. the area of the 2-dimensional surface projected onto the x-y or major plane) is 0.557 square inches. Thus the ratio of the projected surface area of the connector block to the average surface area of the aperture of the windings used in the antenna is 0.557 to 0.258 or 2.159:1, or, put another way, the average surface area of the aperture of the windings used in the antenna is at least equal to 46% of the projected surface area of the connector block. Of course relative sizes other than these may be used. In fact, the present invention includes any such system wherein the average surface area of the aperture of the windings used in the antenna is equal to or greater than at least approximately 20% of the projected surface area of the connector block.

Figure 3A:
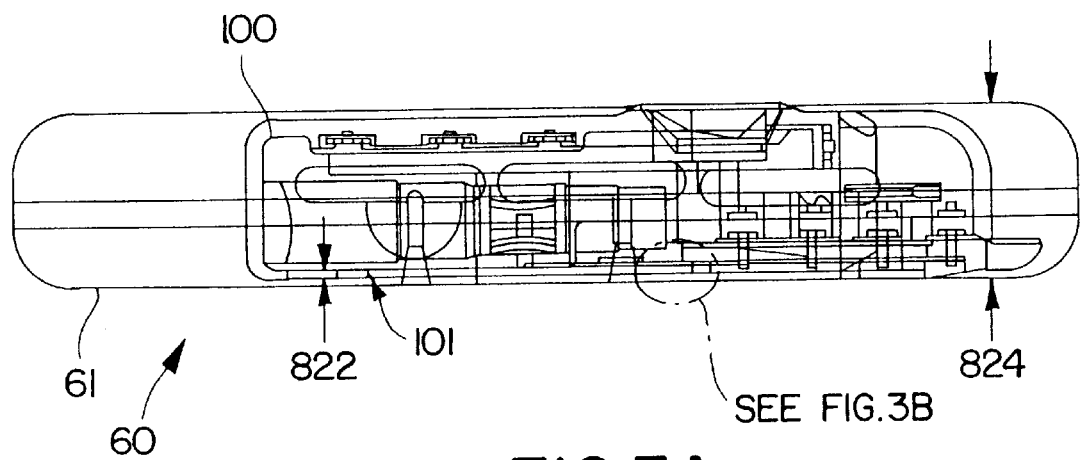
FIG. 3A is a top view of the implantable medical device shown in FIG. 2.
Figure 6A:
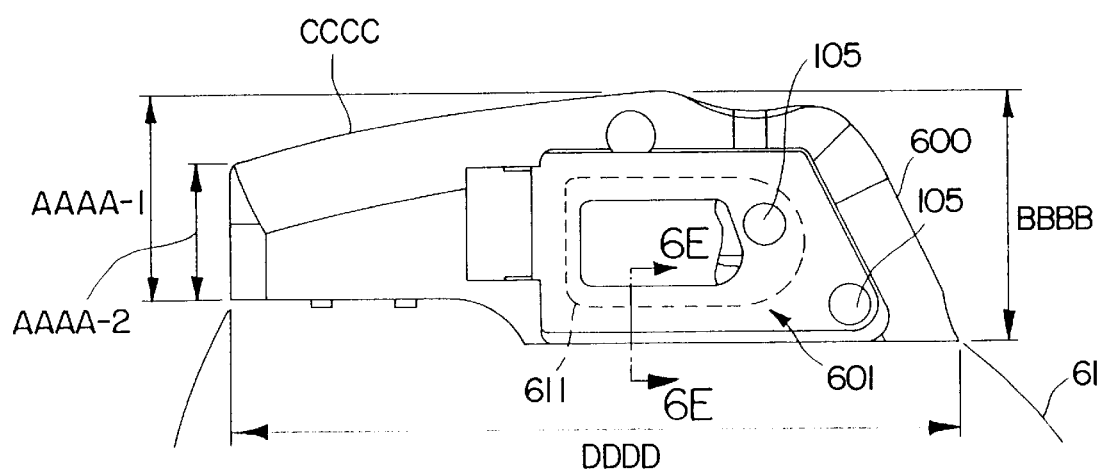
FIGS. 6A–6E depict an alternate embodiment of the present invention.
Figure 6B:
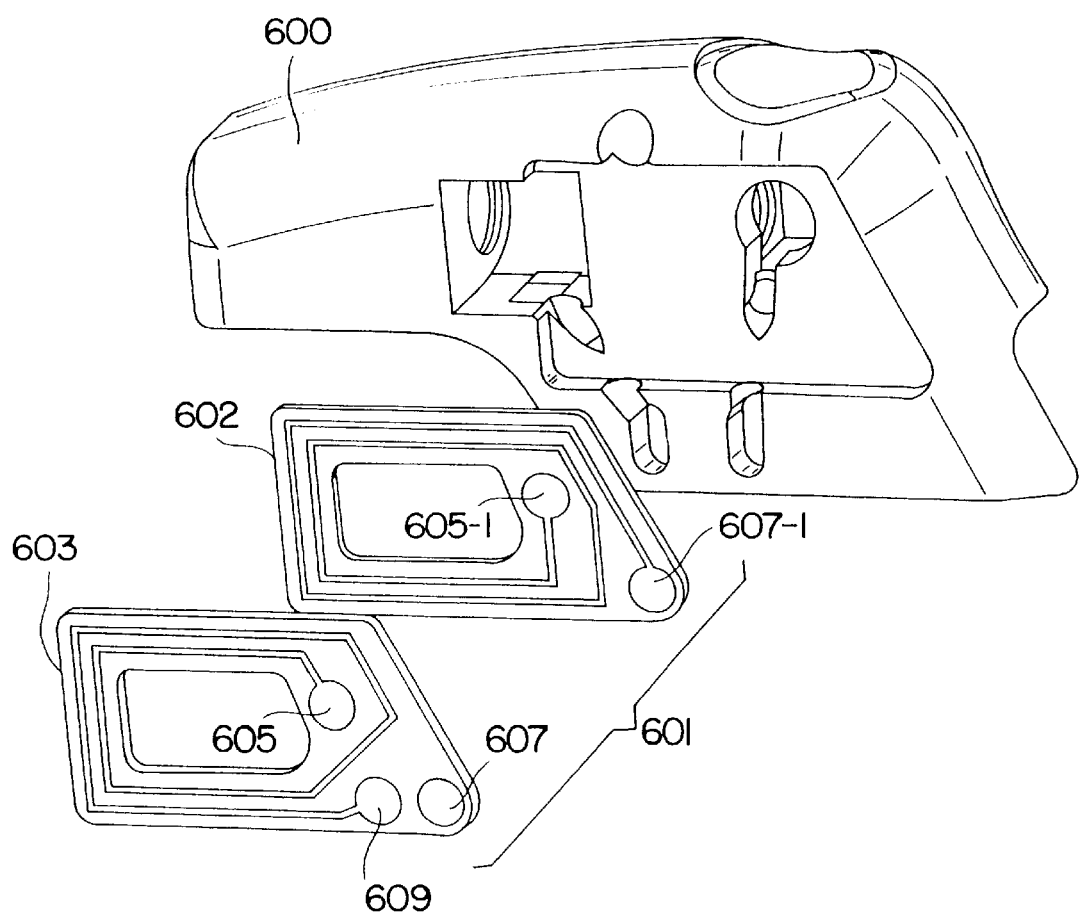
Figures 1, 6C:
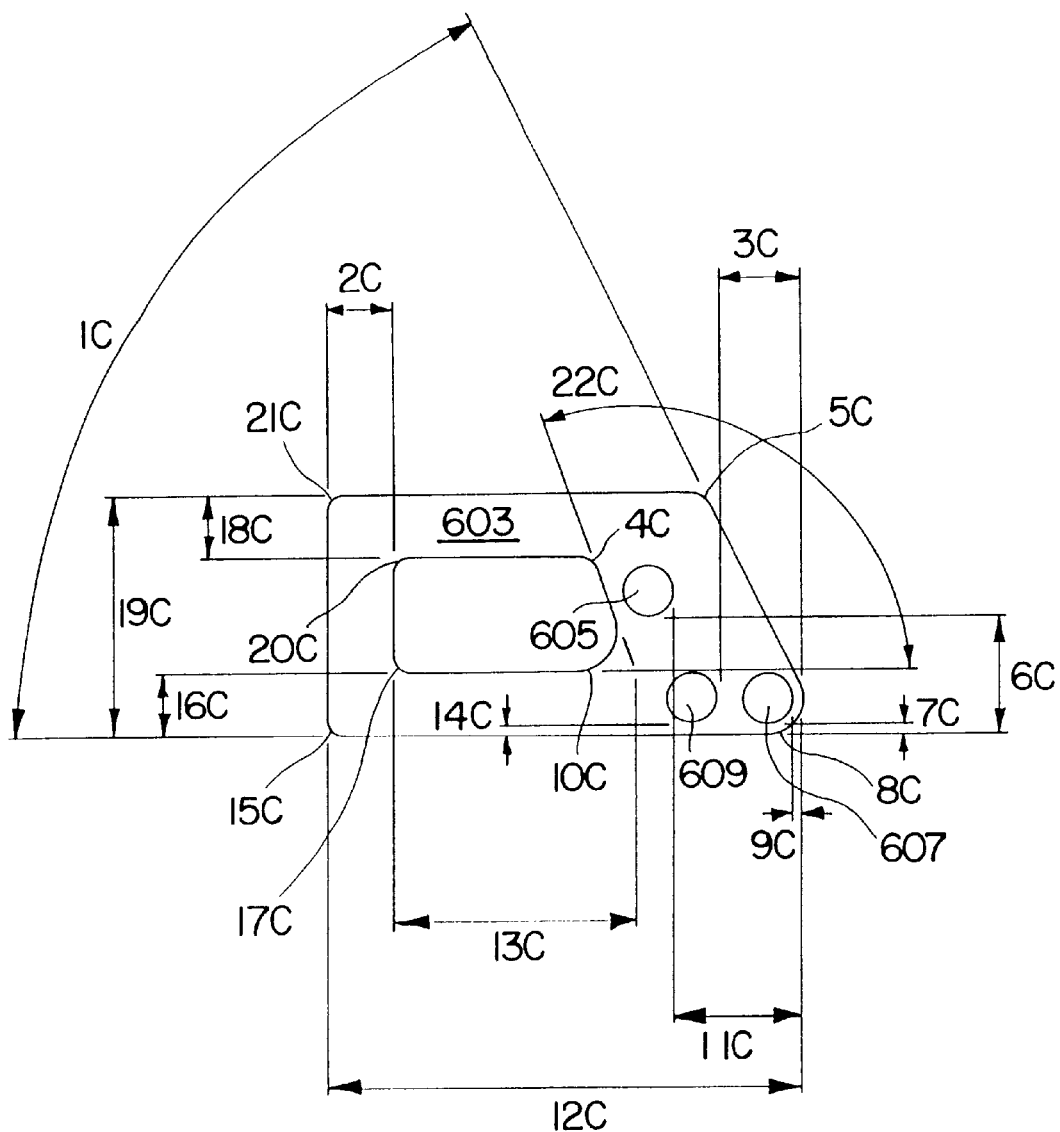
Figures 2, 6C:
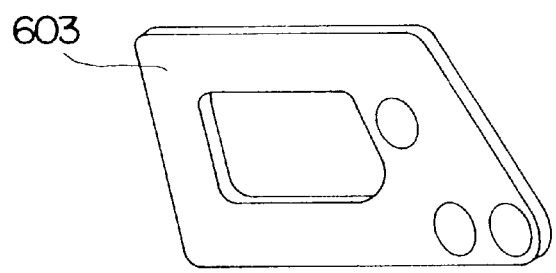
Figures 1, 6D:
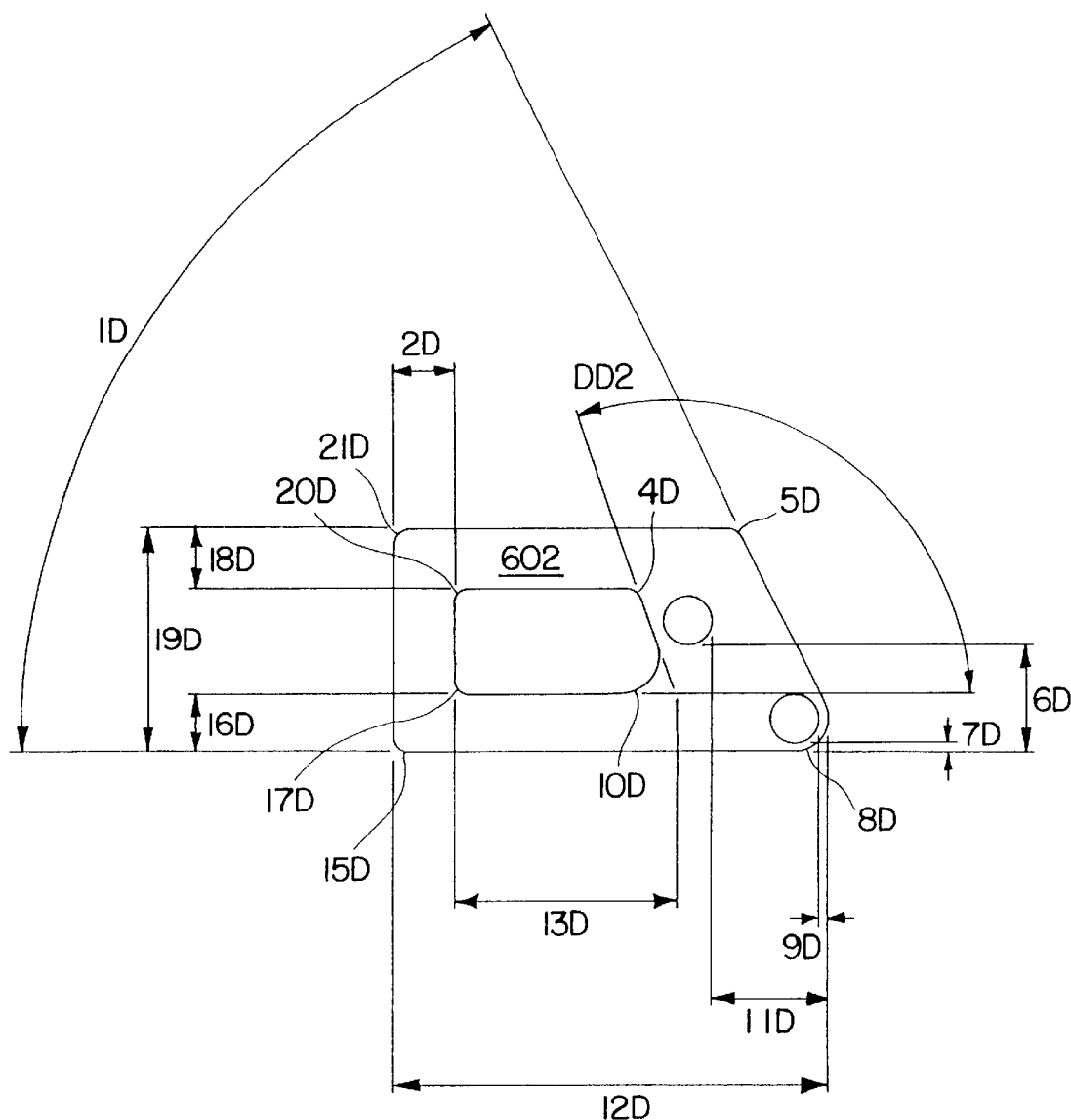
Figures 2, 6D:
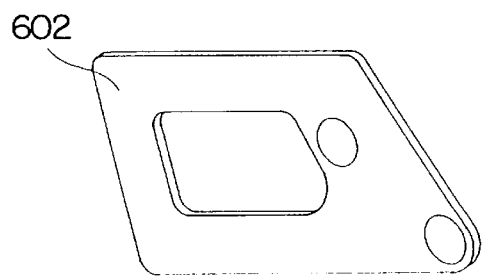

FIG. 3A is a top view of the implantable medical device shown in FIGS. 2.A and B. As seen antenna 101 is positioned within connector block 100 in a manner in which it is parallel to or in the same plane as the major plane of the canister 61. Through this view, the relative thickness of the antenna relative to the connector block and the hermetic housing or canister 61 of device 60 may be appreciated. As seen, canister 61 has a thickness 824 which in the preferred embodiment is 0.312 inches while thickness 822 of antenna is 0.012 inches. Thus the ratio of the thickness of antenna (including the enclosure) to that of the device is 1:26, or, put another way, the thickness of antenna (including the enclosure) is no more than 3.85% of the thickness of the canister of the device. Of course, other relative sizes other than these may further be used. As discussed below, the antenna (windings and the enclosure) may be at least 1000 microns (0.00394 inches) in thickness, in which case, assuming a canister thickness of only 0.0312 inches, the ratio of the thickness of antenna to that of the canister would be 7.92:1, or, put another way, the thickness of the antenna would be no more than approximately 12.62% of the thickness of the canister. Moreover, this percentage will of course also be different if the thickness of the windings used in the antenna relative to the thickness of the device is changed. For example, assuming the thickness of the canister of the device is 5000 microns and the windings of the antenna may be upwards of 1000 microns in thickness, then the thickness of the antenna to that of the device is equal to 20% of the thickness of the device. Thus, the present invention encompasses any device wherein the antenna thickness is equal to or less than approximately 20% of the thickness of the canister of the device.

Figure 3B:
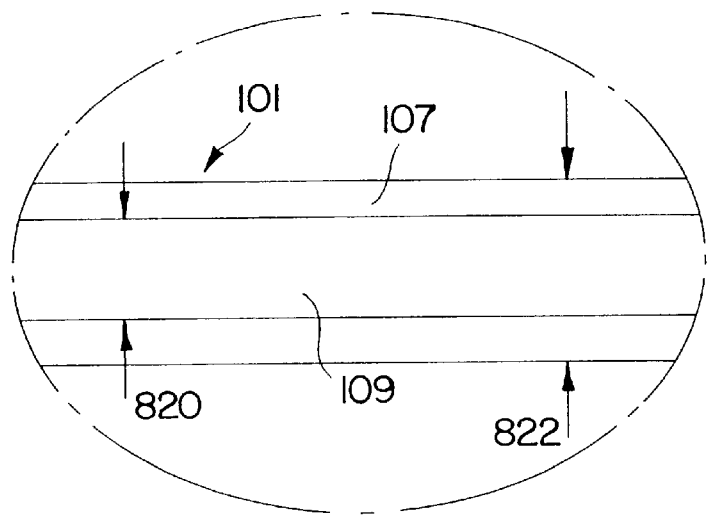
FIG. 3B is a detailed view of the antenna shown in FIG. 3A.

FIG. 3B shows in detail the thickness of the antenna, including the enclosure and the windings. As seen windings used in the antenna have a thickness 820 of 100 microns (0.004 inches) while the total thickness 822 of the antenna, that is the enclosure and windings, is 300 microns (0.012 inches.) In the preferred embodiment the canister has a thickness 824 of 0.312 inches. Of course the thickness of the windings used in the antenna, the enclosure of the windings as well as the canister may all be varied greatly. In fact, the present invention includes any implantable medical device wherein the thickness of the windings used in the antenna is between 1–1000 microns, with 100 microns preferred (0.004 inches.) In terms of the relative thickness of these various components, in the preferred embodiment the ratio of the thickness of the canister to the thickness of the windings used in the antenna in the preferred embodiment is 0.312:0.004 or 78:1, or put another way, the thickness of the windings used in the antenna is no more than 1.28% of the thickness of the canister. This minimal thickness of the antenna is of great importance for an implantable medical device because it permits the ultimate size of the device to be minimized. In the present illustration the minimal thickness means the antenna may be positioned within the connector block without hindering the connection of the leads into the device, i.e. the lead plugs are not obstructed by the antenna, although in alternate embodiments the antenna may likewise be positioned within the canister. Of course, other thicknesses of each component may also be used. The present invention contemplates any ratio of antenna thickness to canister thickness between approximately 1:15 and 1:1000 and a ratio of thickness of the windings used in the antenna to the canister thickness between approximately 1:7.8 to 1:7800. Moreover, although shown here mounted within the connector block, the antenna may be mounted wherever desired, such as within the canister itself.

Figure 4A:
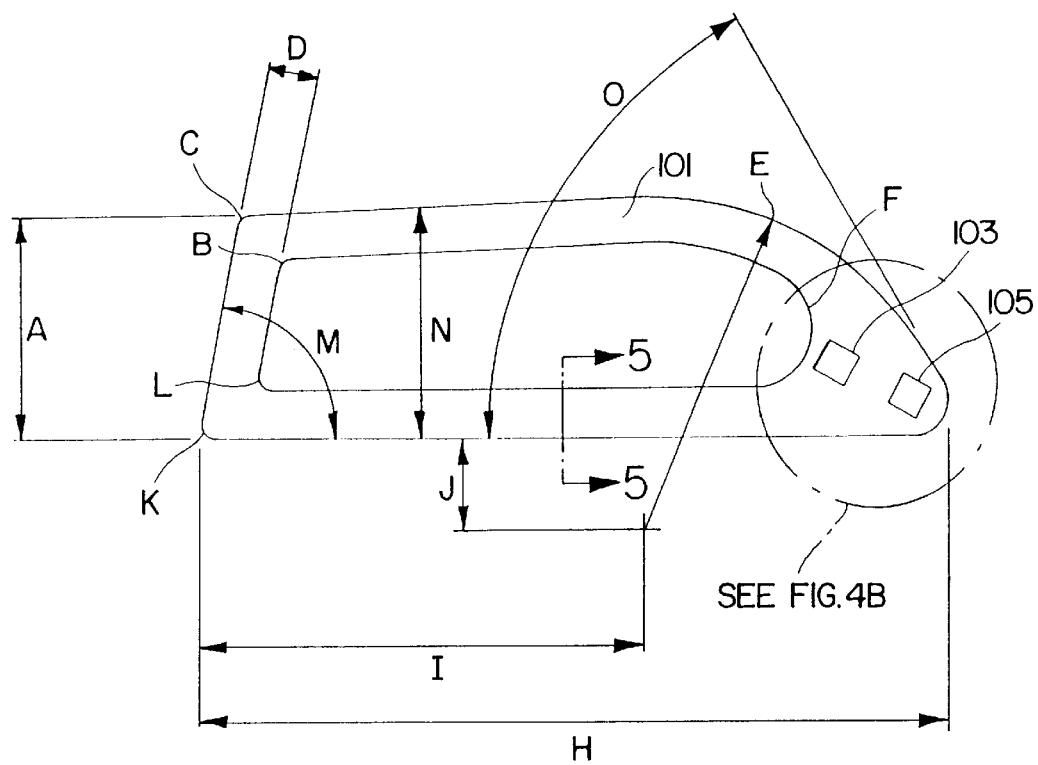
FIG. 4 is a detailed view of the antenna used in the implantable medical device shown in FIG. 2.
Figure 4B:
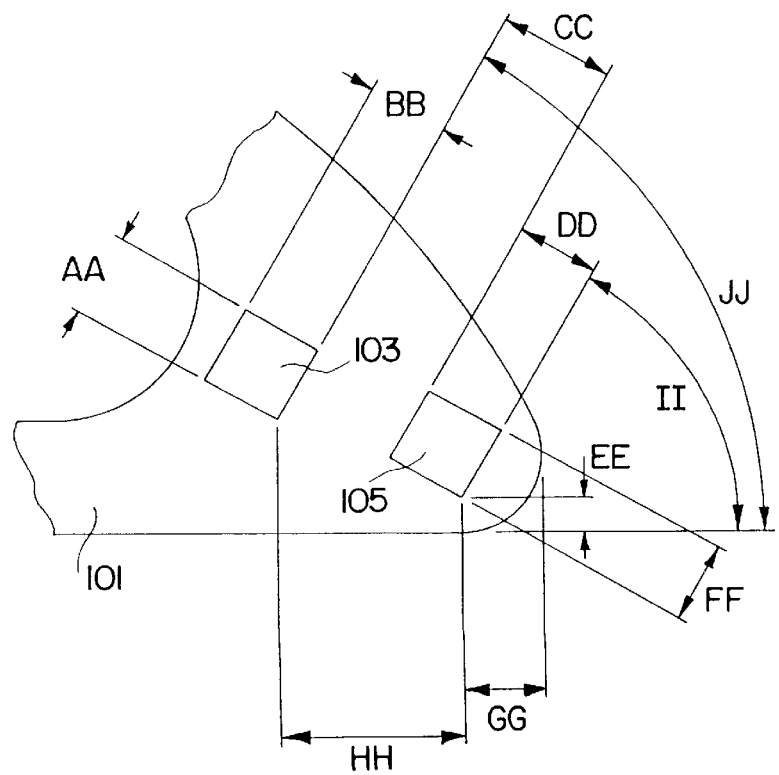
Figure 5:
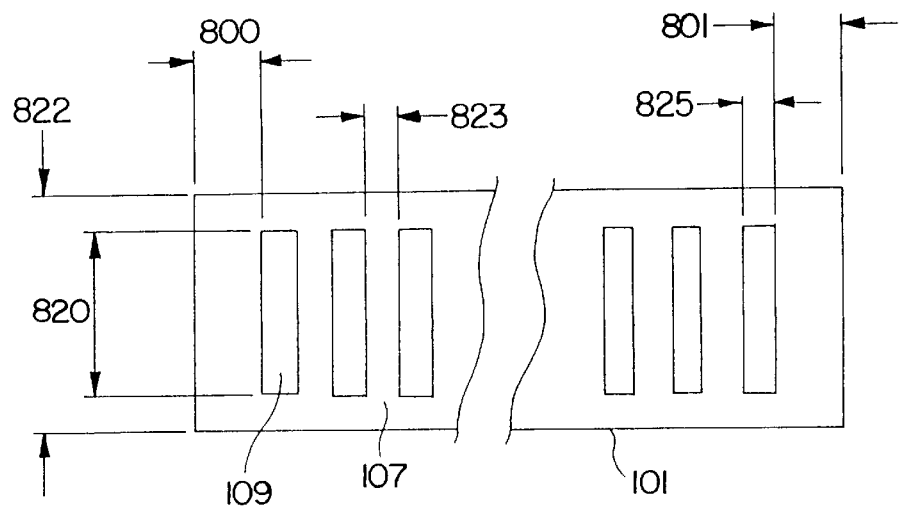
FIG. 5 is a cross sectional view of the antenna in FIG. 4

FIG. 4 is a detailed view of the antenna 101 used in the preferred embodiment. As seen antenna has two contact pads 103, 105 which respectively couple opposite ends of the winding 109 with device. Antenna 101 has the following dimensions: A=8.64 millimeters; B=0.51 millimeters radius; C=0.50 millimeters radius; 1.78 millimeters; E=12.7 millimeters; F=2.29 millimeters radius; G=1.27 millimeters radius; H=28.53 millimeters; 1=16.81 millimeters; J=3.49 millimeters; K=0.51 millimeters radius; L=0.51 millimeters radius; M=80 degrees; N=2.20 degrees; O=60.0 degrees; AA=1.27 millimeters; BB=1.27 millimeters; CC=1.78 millimeters; D1.27 millimeters; EE=0.56 millimeters; FF=1.27 millimeters; GG=1.27 millimeters; HH=2.79 millimeters; II=60 degrees and JJ=60 degrees;

FIG. 5 is a cross sectional view of the antenna in FIG. 4. As better seen in this view, antenna 101 is constructed from an enclosure 107 which has mounted within a series of windings 109. In the preferred embodiment, the enclosure is constructed from polycarbonate and the windings are gold, although other materials may be used for each. For example, the enclosure could be medical adhesive and the windings copper or platinum or niobium. The antenna preferably consists of a single winding of a conductive material having 30 turns, although more or less turns may be used, depending on the application for the antenna and the telemetry system used. For example, it is within the scope of the present invention for the antenna to have a series of up to 1000 turns of a conductive material. The conductive material preferably is rectangular in cross section, although other shapes, such as square, round or even C-shaped, for example, may also be used. The winding, moreover preferably lies in a single flat plane. Only a single winding of a conductive material or multiple windings may be used. Each winding may be between approximately 1–100 microns wide 825, between approximately 1–1000 microns thick 820 with each turn spaced apart 823 from each of the other turns between approximately 1–100 microns. The winding is preferably mounted within enclosure 107 having a thickness 822 of between approximately 100–1500 microns. Of course, the antenna may be used without being mounted within an enclosure. In the preferred embodiment the conductive material used for the winding is rectangular in cross section, 100 microns thick 820 and 25 microns wide 825, thus having a thickness to width aspect ration of 4:1. Each turn of the winding is preferably spaced apart 823 from each of the other turns by 20 microns. In the preferred embodiment the enclosure of the antenna is 300 microns or 0.012 inches thick 822 . Of course other relative sizes other than these may be used including windings have an aspect ratio between approximately 1000:1 as well as non-rectangular shapes.

FIG. 6A depicts an alternate embodiment of the present invention. In particular in this embodiment the relative size of the antenna 601 compared to the connector block 600 in a single chamber device is shown. As discussed above a single chamber devices differs from a dual chamber device in that only a single lead is coupled or plugged into the connector block. Consequently in single chamber devices the connector block tends to be smaller in size as compared to dual chamber devices. As seen connector block has the following dimensions: AAAA—1 is 0.305 inches; AAAA—2 is 0.205 inches; BBBB is 0.375 inches, CCCC is 2.6 inches in radius and DDDD is 1.061 inches. The average aperture 611 of the windings used in the antenna may be determined by averaging the inner and outer surface areas of the antenna. As seen antenna (the term which as used here includes both the windings and the enclosure) has an outer surface area of 0.124 square inches and an inner surface area of 0.029 square inches. Thus the average surface area of the aperture of the windings used in the antenna is 0.077 square inches. The antenna is positioned within the connector block. In the preferred embodiment, the projected surface area of the connector block (i.e. the surface area within its major plane) is 0.311 square inches. Thus the ratio of the surface area of the connector block to the average surface area of the aperture of the windings used in the antenna is 0.311 to 0.077 or 4.039:1, or, put another way, the average surface area of the aperture of the windings used in the antenna is at least equal to approximately 24.76% of the projected surface area of the connector block. Of course, other relative sizes other than these may further be used. In fact, the present invention includes any such system wherein the average surface area of the aperture of the windings used in the antenna is equal to or greater than at least approximately 20% of the surface area of the connector block. In addition, the present invention includes any such system wherein the average surface area of the aperture of the windings used in the antenna is equal to or greater than approximately 0.01 square inches. Moreover, due to the smaller size of the overall connector block in this embodiment two planar antenna are stacked together as seen in FIG. 6B.

As seen in FIG. 6B antenna 601 is constructed by stacking and laminating together two planar antenna components 602 and 603. As seen, the windings of each component are electrically coupled through contact pads 605 and 605—1 as well as 607 and 607—1.

FIGS. 6C-1, 6C-2 and 6D-1, 6D-2 disclose the various dimensions of the antenna 601 and in particular of the two planar antenna components 602 and 603. The component 602 in FIGS. 6C-1 and 6C-2 has the following dimensions: 1C=64 degrees; 2C=1.78 mm; 3C=2.29 mm; 4C=0.51 radius mm; 5C=0.51 radius mm; 6C=3.33 mm; 7C=0.25 mm; 8C=1.02 radius mm; 9C=0.25 mm; 10C=1.27 radius mm; 11C=3.48 mm; 12C=12.85 mm; 13C=6.58 mm; 14C=0.25 mm; 15C=0.51 radius mm; 16C=1.78 mm; 17C=0.51 radius mm; 18C=1.78 mm; 19C=6.86 mm; 20C=0.51 radius mm; 21C=0.51 radius mm; 22C=110 degrees. The component 603 in FIGS. 6D-1, and 6D-2 has the following dimensions: 1D=64 degrees; 2D=1.78 mm; 3D=not used in this figure; 4D=0.51 radius mm; 5D=0.51 radius mm; 6D=3.33 mm; 7D=0.25 mm; 8D=1.02 radius mm; 9D=0.25 mm; 10D=1.27 radius mm; 11D=3.48 mm; 12D=12.85 mm; 13D=6.58 mm; 14D= not used in this figure; 15D=0.51 radius mm; 16D= 1.78 mm; 17D=0.51 radius mm; 18D=1.78 mm; 19D=6.86 mm; 20D=0.51 radius mm; 21D=0.51 radius mm; 22D=110 degrees.

Figure 6E:
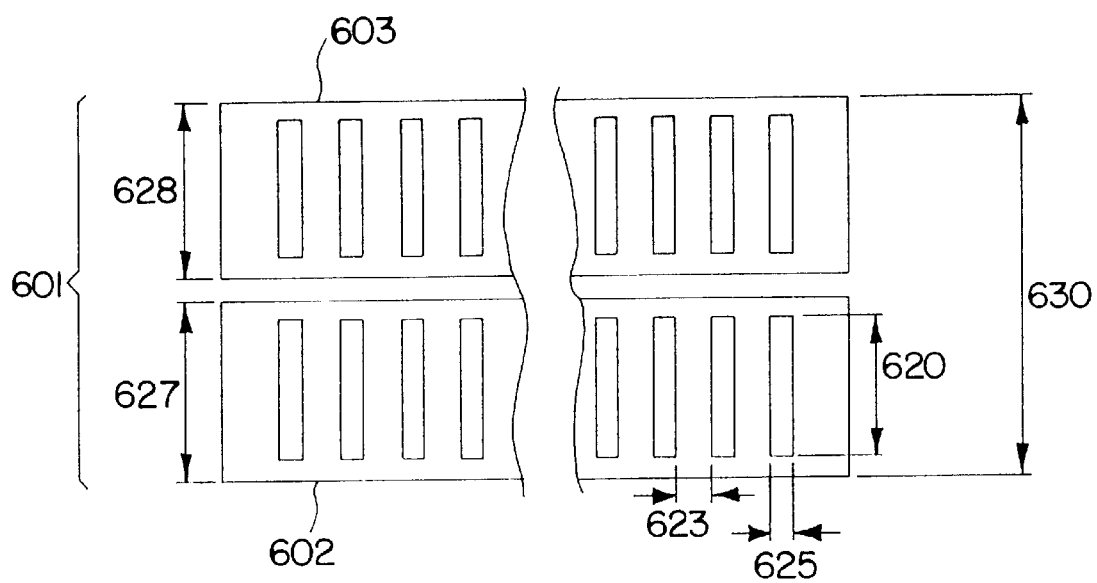

FIG. 6E is a sectional view of the antenna 602 shown in FIG. 6A. As seen antenna is constructed from antenna components 602 and 603. In the preferred embodiment each component has a series of 30 windings, with each winding being 25 microns wide 625 and 100 microns thick 620 and is spaced apart 623 at 20 microns. Each enclosure of antenna components 602 and 603 is 0.012 inches or 300 micron thick 627, 628. The total thickness 630 of antenna components 602 and 603 when laminated together is 0.020 inches. Lamination is accomplished by any suitable biocompatible glue, although other methods of joining, such as melting, may also be used. Of course all the dimension thus listed may be altered and tailored to the specific requirements of the implantable device. For example, more or less windings or layers of conductive material may be used, depending on the application for the antenna and the telemetry system used. Each winding moreover, may be in the range of between approximately 1–100 microns wide, in the range of between approximately 1–1000 microns thick and spaced apart from each of the other windings in the range of between approximately 1–100 microns. The winding may or may not be mounted within any suitably sized enclosure. Moreover, any number of turns of conductive material in the range of approximately between approximately 1 to 1000 may be provided within each winding. Finally although depicted on parallel planes, each winding may be provided on intersecting planes, if desired (perpendicular or canted.)

Figure 7:
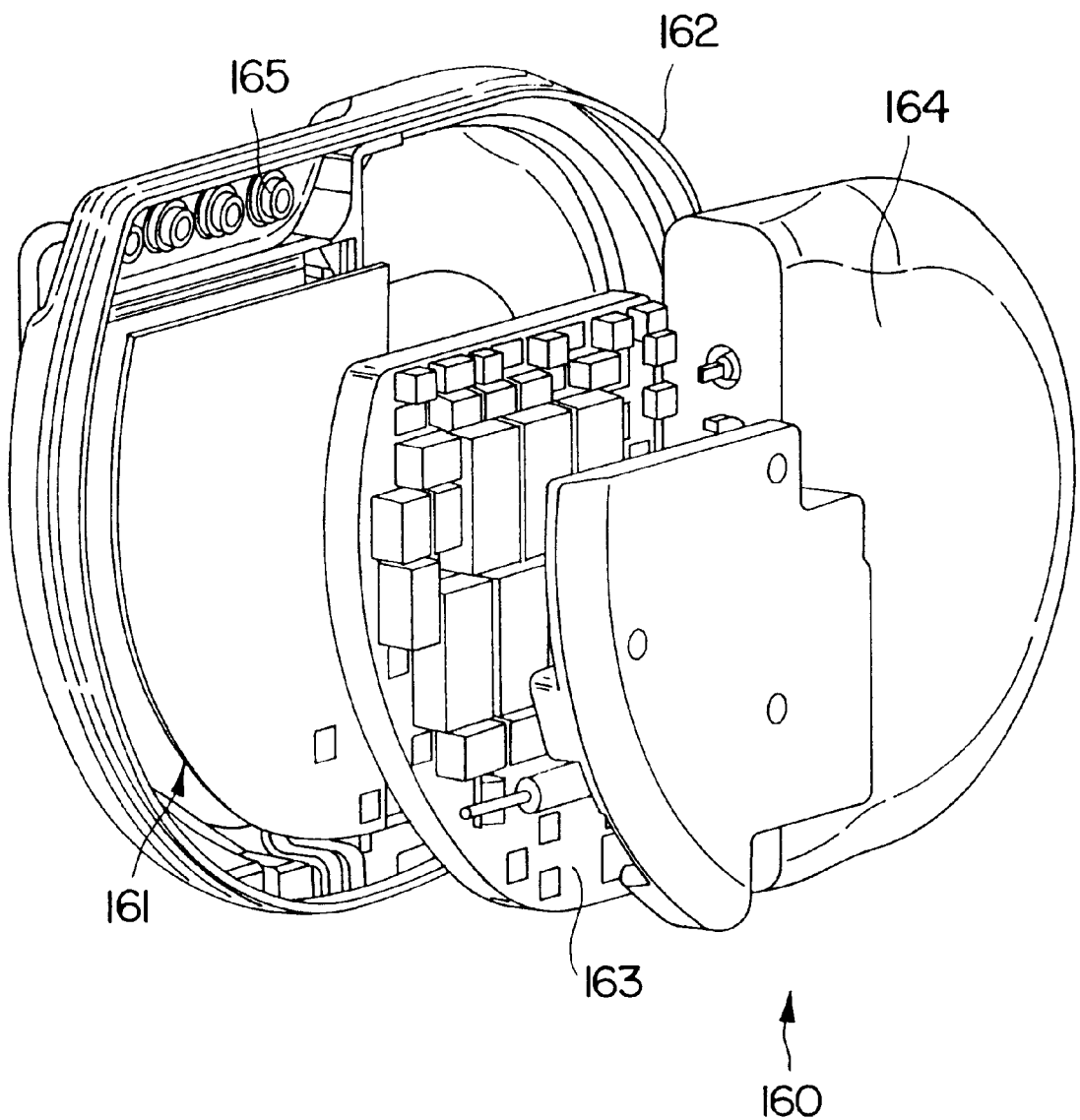
FIG. 7 depicts an alternate embodiment of the present invention.

FIG. 7 depicts an alternate embodiment of the present invention. In particular, in this embodiment an antenna 161 is housed within the hermetic canister 162 of the device 160. The hermetic canister may be made of a biocompatible ceramic material, such as 99.8% aluminum oxide. As seen, hermetic canister consists of two halves (only one of which is shown in this FIG.). Inside the canister is positioned an electronic module 163 which includes the device electronics and pulse generator system. Module is electrically coupled to battery 164 and to feedthroughs 165. As discussed above the feedthroughs electrically couple the interior components to the connector block assembly (not shown in this FIG.). Also coupled to the electronic module is the antenna 161. Antenna is constructed in a similar fashion to that discussed above, wherein the conductive material winding is in the range of approximately 1–100 microns wide, in the range of approximately 1–1000 microns thick, and is wound as a series of turns in the range of approximately between approximately 1–1000 turns spaced in the range of approximately between approximately 1–50 microns apart, moreover although two layers are shown, any number of layers or winding greater than one may also be used. In this embodiment antenna preferably has these characteristics: two layers electrically coupled together, each layer having a single winding of a conductive material which is 25 microns wide, 100 microns thick, and is wound as a series of 30 turns concentric and within a single plane which are spaced 20 microns apart. In the preferred embodiment gold is used as the conductive material.

Figure 8A:
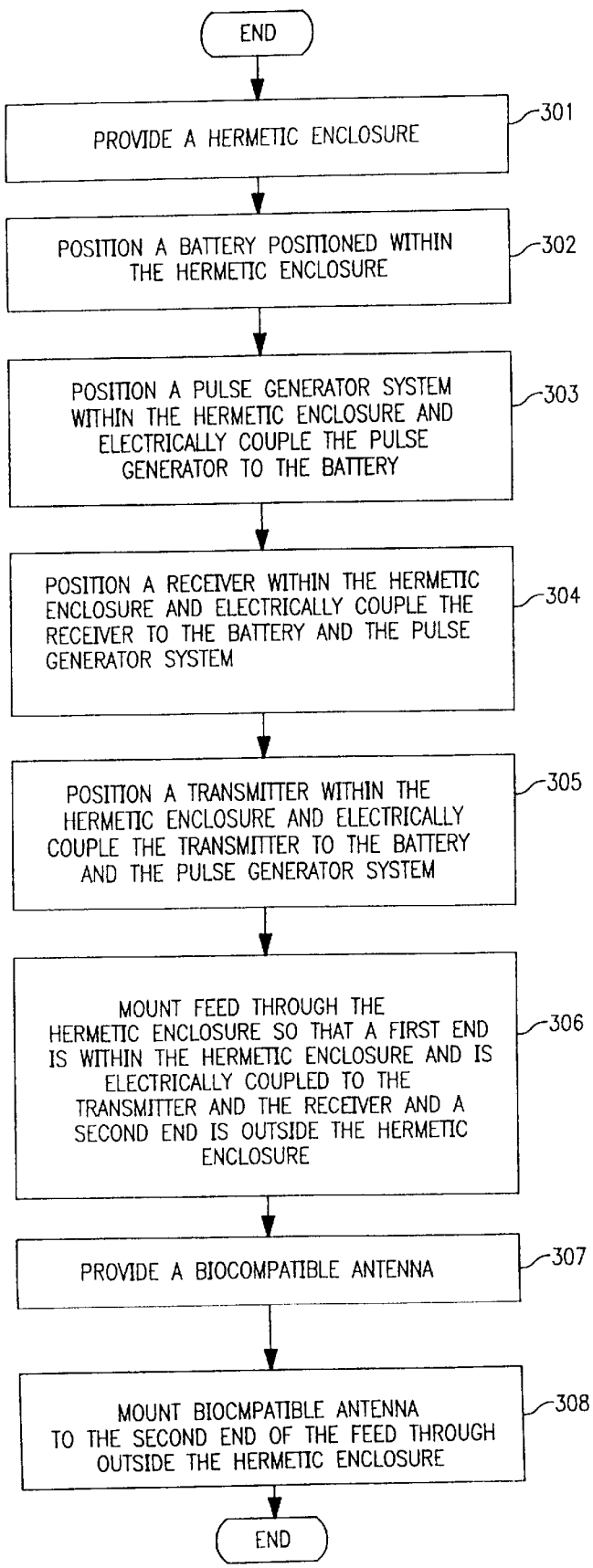
FIG. 8A is a flowchart illustrating the steps used to manufacture an implantable medical device as depicted in FIG. 2.

FIG. 8A is a flowchart illustrating the steps used to manufacture an implantable medical device as depicted in FIG. 2. Step 301 consists of providing a hermetic canister or enclosure. Next, in step 302, positioning a battery within the hermetic canister. Next, in step 303, positioning a pulse generator system within the hermetic canister and electrically coupling the pulse generator to the battery. Next, in step 304, positioning a receiver within the hermetic canister and electrically coupling the receiver to the battery and the device electronics and pulse generator system. Next, in step 305, positioning a transmitter within the hermetic canister and electrically coupling the transmitter to the battery and the pulse generator system. Next, in step 306, mounting feedthrough through the hermetic canister so that a first end is within the hermetic canister or canister and is electrically couple to the transmitter and the receiver and a second end is outside the hermetic canister. Next, in step 307, providing a biocompatible antenna. Finally, in step 308, mounting to the second end of the feedthrough the biocompatible antenna outside the hermetic canister.

Figure 8B:
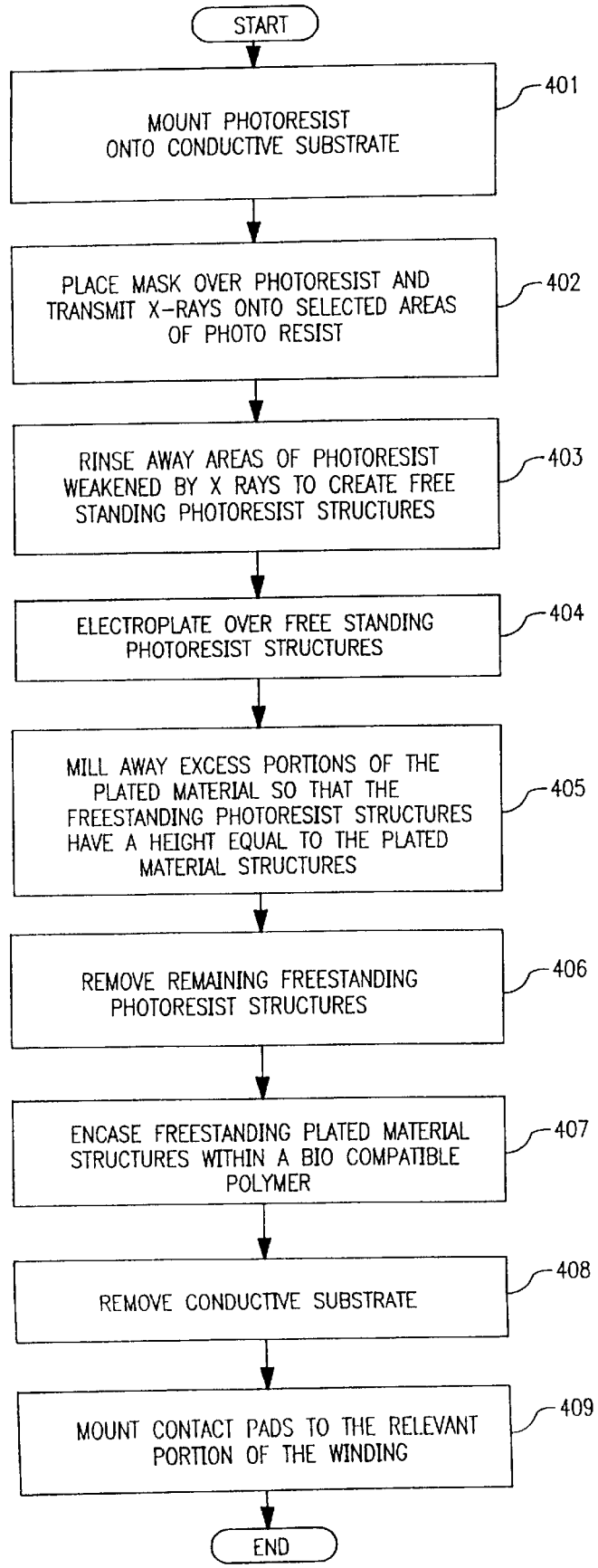
FIG. 8B is a flowchart depicting the steps used to manufacture or provide a biocompatible antenna in a step depicted in FIG. 8A FIGS. 9A–9H illustrate the manufacturing steps discussed above with regards to FIG. 8B The drawings are not necessarily to scale.

FIG. 8B is a flowchart depicting the steps used to manufacture or provide a biocompatible antenna in step 307 discussed above. Step 401 consists of mounting a photoresist onto conductive substrate. Next, in step 402, placing mask over photoresist and transmit x-rays onto selected areas of photo resist. Next, in step 403, rinsing away areas of photoresist weakened by x rays to create free standing photoresist structures. Next, in step 404, electroplating over free standing photoresist structures. Next, in step 405, milling away excess portions of the plated material so that the freestanding photo resist structures have a height equal to the plated material structures. Next, in step 406, removing remaining freestanding photo resist structures. Next, in step 407, encasing freestanding plated material structures within a biocompatible polymer. Next, in step 408, removing conductive substrate. Finally, in step 409, mounting contact pads to the relevant portion of the winding to create a biocompatible antenna.

FIG. 9 illustrates the manufacturing steps discussed above with regards to FIG. 8b. As seen, in FIG. 9A in the first step a photo resist 901 is mounted onto a conductive substrate 902. In the preferred embodiment photo resist is PMMA and conductive substrate is titanium.

Figure 9A:
Figure 9B:
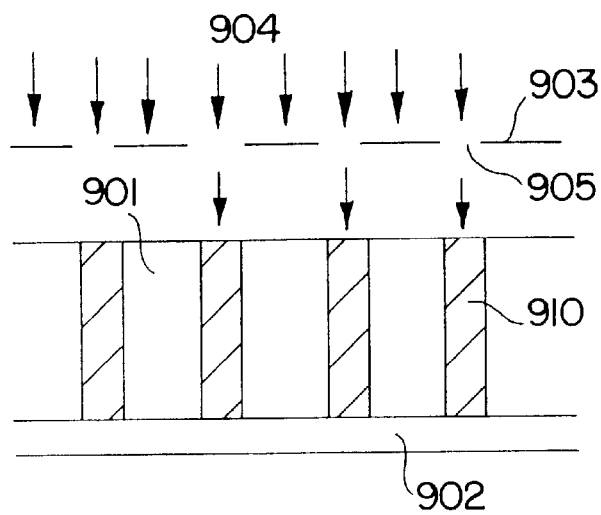

Next, as seen in FIG. 9B, a mask 903 is placed over the photo resist. X rays 904 transmitted from a device (not shown) above the mask passes through apertures 905 in the mask and weakens those exposed areas of the photo resist. Once exposed the weakened areas 910 of the photo resist are rinsed away with a developer so that freestanding structures of photo resist remain. In the preferred embodiment the X-rays are transmitted from any acceptable source, such as a synchrotron, the mask is chrome and the developer is acetone.

Figure 9C:
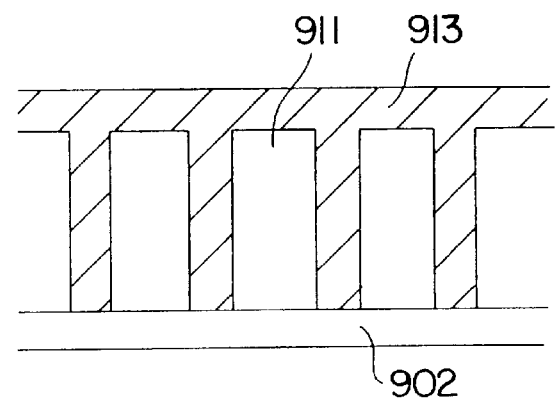

Next, as seen in FIG. 9C, a material 913 is electroplated over the free standing photoresist structures 911. In the preferred embodiment the material is gold. Other biocompatible materials may also be used such as platinum or tantalum. The electroplating may be accomplished in any acceptable manner. In addition other forms of depositing a material may also be used, such as sputtering. Of course, if other deposition methods are used the substrate need not necessarily be conductive.

Figure 9D:
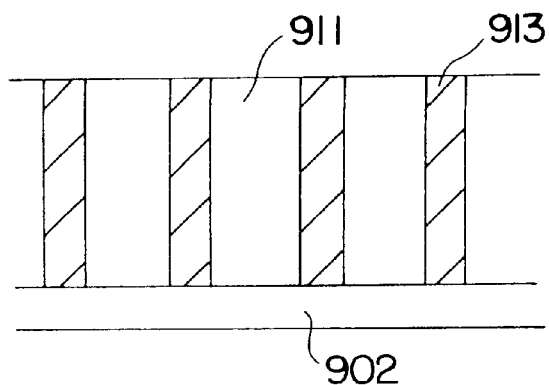

Next, as seen in FIG. 9D, a milling step is performed. As seen during this step the excess portions of the plated material are mechanically removed so that the freestanding photo resist structures 911 have a height equal to the plated material structures 913 deposited in between approximately. Milling may be accomplished in any acceptable manner and is typically performed using a mechanical process in which an abrasive material is used to remove the plated material.

Figure 9E:
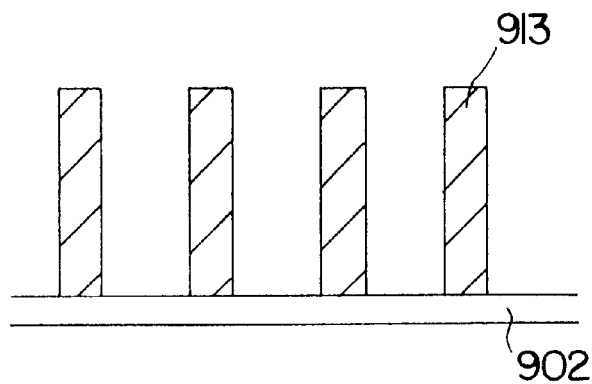

Next, as seen in FIG. 9E, the freestanding photo resist structures 911 are removed. In the first embodiment this removal step is accomplished with a solvent such as acetone. Of course, the solvent used would depend upon be material used for the photo resist.

Figure 9F:
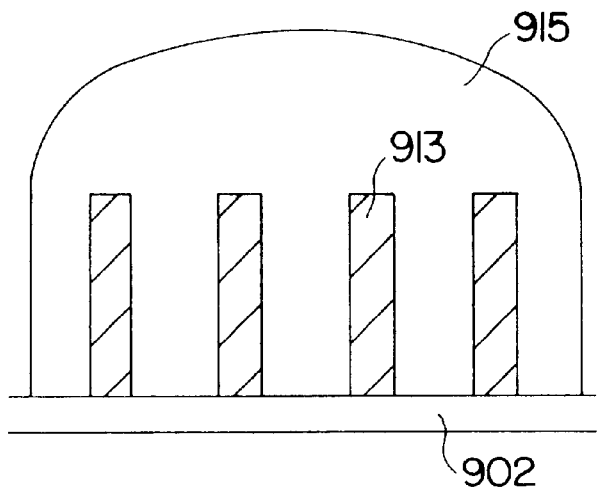

Next, as seen in FIG. 9F, the freestanding plated structures 913 are encased within a biocompatible polymer 915. In the preferred embodiment polycarbonate is used although other materials, such as epoxy polyurethane or polyester may also be used. The encasement is accomplished under heat and pressure so as to completely encase, without any voids, all of the freestanding plated pleaded structures.

Figure 9G:
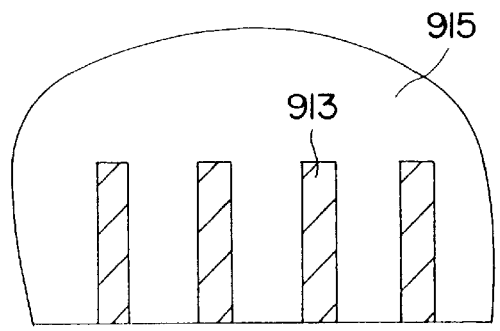

Next, as seen in FIG. 9G, the conductive substrate 902 is removed. In the preferred embodiment this is accomplished by first cooling the conductive substrate with liquid nitrogen and then peeling it away from the plated material structures 913.

Figure 9H:
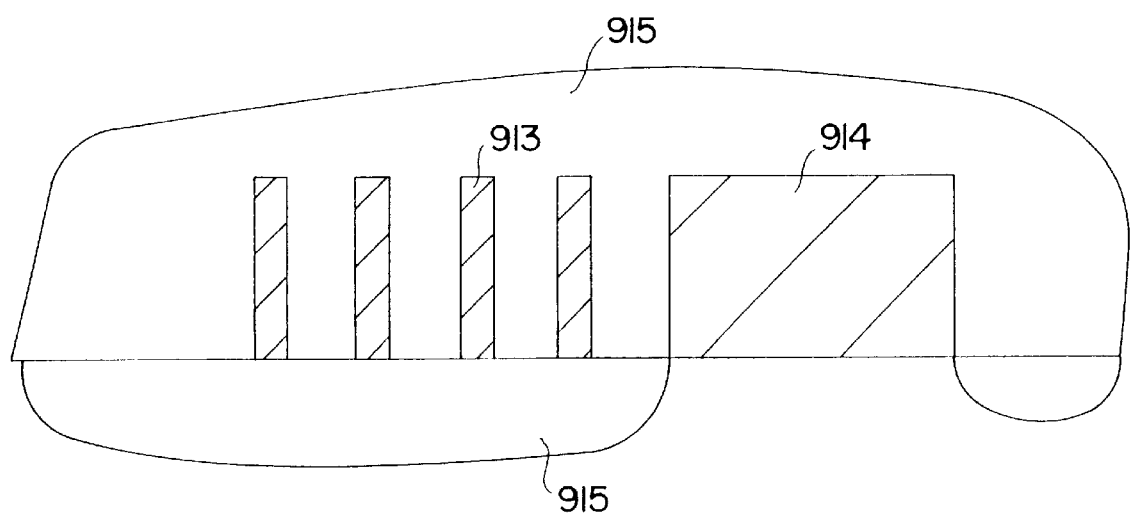

Next, as seen in FIG. 9H, contact pads 914 are placed at the relevant portion of the winding. Finally the entire structure other than the contact pads are further encased so as to be fully enclosed within the biocompatible polymer.

From these steps an antenna which is thus completely encased within biocompatible polymer but which is made of very small structures having a high aspect ratio and which are moreover made from a completely biocompatible and biostable material, such as gold, may be produced.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein. For example, although shown in the context of a battery powered device, the disclosed antenna may also be used in device not directly powered by batteries, e.g. RF powered device or movement powered devices. Moreover although shown within the context of a planar, single winding antenna, the present invention may be also used to provide antennas having multiple windings (e.g. 2, 3, 4, etc.) or even antennas having complex shapes or geometries (e.g. conical or helical.) It thus must be understood the present invention encompasses a much broader scope of embodiments than merely those disclosed herein.

What is claimed is:

1. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and an antenna positioned outside the hermetic canister and coupled to the pulse generator;

wherein the first winding is in the range of approximately 1–100 microns wide, in the range of approximately 1–1000 microns thick, the first winding has a series of between approximately 1–1000 turns spaced between approximately 1–50 microns apart.

2. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and an antenna positioned outside the hermetic canister and coupled to the pulse generator, the antenna having a first winding of a conductive material, the first winding lying substantially in a first plane, the first winding comprising a first series of turns about a first axis, the first axis being perpendicular to the first plane;

wherein each winding has a cross sectional shape, the cross sectional shape being rectangular.

3. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and an antenna positioned outside the hermetic canister and coupled to the pulse generator;

wherein the antenna has a first winding of a conductive material, the conductive material having a cross section, the cross section having an aspect ratio between the range of approximately 1:1 to 1:1000.

4. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and an antenna positioned outside the hermetic canister and coupled to the pulse generator;

wherein the antenna has a first winding of a conductive material, the first winding lying substantially in a first plane, the first winding comprising a first series of turns about a first axis defining a first average aperture of the windings used in the antenna within the first plane, the first average aperture of the windings used in the antenna within the first plane having a first average aperture of the windings surface area which is greater than approximately 0.01 square inches.

5. An implantable medical device of claim 4 wherein the first average aperture of the windings surface area is equal to approximately 0.077 square inches.

6. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and a first planar antenna and a second planar antenna positioned outside the hermetic canister, the first planar antenna being coupled to the pulse generator, the second planar antenna being electrically coupled to the first planar antenna, the second planar antenna being positioned outside the hermetic canister, a connector block being coupled to the hermetic enclosure, the first planar antenna and the second planar antenna being positioned within the connector block.

7. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and a first planar antenna positioned outside the hermetic canisters the first planar antenna being coupled to the pulse generator;

wherein a connector block is coupled to the hermetic enclosure, the first planar antenna component having a first winding of a conductive material, the first winding comprising a first series of turns lying substantially in a first plane, the first series of turns defining a first average aperture of the windings, the first average aperture of the windings having a first surface area, the connector block having a connector block surface area within the first plane, the first surface area being equal to or greater than at least approximately 20% of the connector block surface area.

8. An implantable medical device of claim 7 wherein the average surface area of the aperture of the windings used in the antenna is equal to or greater than at least 20% of the surface area of the connector block.

9. An implantable medical device of claim 7 wherein the average surface area of the aperture of the windings used in the antenna is approximately equal to or greater than approximately 50% of the surface area of the connector block.

10. An implantable medical device, comprising:

an hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and a first planar antenna positioned outside the hermetic canister, the first planar antenna having a thickness and being coupled to the pulse generator, the antenna thickness being equal to or less than approximately 20% of the thickness of the device.

11. An implantable medical device comprising:

a hermetic canister;

a battery positioned within the hermetic canister;

a pulse generator system positioned within the hermetic canister and electrically coupled to the battery;

a receiver positioned within the hermetic canister and electrically coupled to the battery and the pulse generator system;

a transmitter positioned within the hermetic canister and electrically coupled to the battery and the pulse generator system; and an antenna coupled to the transmitter and the receiver, the antenna having a first winding of a conductive material, the first winding comprising a first series of turns lying substantially in a first plane, the first series of turns defining a first average aperture of the windings, the first average aperture of the windings having a first surface area, the first surface area greater than approximately 0.01 square inches.

12. An implantable medical device of claim 11 wherein the first surface area is greater than approximately 0.07 square inches.

13. An implantable medical device of claim 11 wherein the first surface area is greater than approximately 0.2 square inches.

14. An implantable medical device of claim 11 further comprising a connector block coupled to the hermetic canister, the connector block having a surface area in the first plane wherein the antenna is mounted to the connector block.

15. An implantable medical device of claim 11 wherein the surface area of the connector block within the first plane is approximately 0.557 square inches.

16. An implantable medical device of claim 11 wherein the ratio of the surface area of the connector block to the first surface area is no more than 2.159:1.

17. An implantable medical device of claim 11 wherein the average surface area of the aperture of the windings used in the antenna is equal to or greater than at least approximately 20% of the surface area of the connector block.

18. An implantable medical device of claim 11 wherein the first surface area is at least equal to approximately 46% of the projected surface area of the connector block.

19. An implantable medical device of claim 18 wherein the thickness of antenna is no more than approximately 3.85% of the thickness of the canister of the device.

20. An implantable medical device of claim 11 wherein the antenna has a thickness in a first direction, the hermetic canister has a thickness in the first direction wherein the thickness of the antenna is equal to or less than approximately 20% of the thickness of the canister.

21. An implantable medical device of claim 20 wherein the thickness of the antenna would be no more than approximately 12.62% of the thickness of the canister of the device.

22. An implantable medical device of claim 11 wherein the windings used in the antenna have a thickness no more than approximately 1000 microns.

23. An implantable medical device of claim 11 wherein the antenna is positioned within the connector block.

24. An implantable medical device of claim 11 wherein the ratio of antenna thickness to canister thickness is between approximately 1:15 and 1:1000 and the ratio of thickness of the windings used in the antenna to the canister thickness is between approximately 1:7.8 and 1:7800.

25. An implantable medical device of claim 24 wherein the antenna is constructed from an enclosure which has mounted within a first winding.

26. An implantable medical device of claim 25 wherein the enclosure is polycarbonate or polyester or polyurethane or epoxy.

27. An implantable medical device of claim 26 wherein the enclosure is medical adhesive and the conductive material is copper or niobium or platinum.

28. An implantable medical device of claim 11 wherein the conductive material is gold.

29. An implantable medical device of claim 11 wherein the antenna has a first winding having a series of approximately 30 turns.

30. An implantable medical device of claim 11 wherein the first winding is between approximately 1–100 microns wide.

31. An implantable medical device of claim 30 wherein the first winding is approximately 25 microns wide.

32. An implantable medical device of claim 11 wherein the first winding is between approximately 1–1000 microns thick.

33. An implantable medical device of claim 32 wherein the first winding is approximately 100 microns thick.

34. An implantable medical device of claim 11 wherein the turns within the first winding are spaced apart between approximately 1–100 microns.

35. An implantable medical device of claim 34 wherein the turns within the first winding are spaced apart approximately 20 microns.

36. An implantable medical device of claim 11 wherein the first winding has an aspect ratio between approximately 1–1000:1.

37. An implantable medical device of claim 36 wherein the first winding has an aspect ratio between 1:1 and 10:1.

38. An implantable medical device of claim 11 wherein the first winding is rectangular in cross section.

39. An implantable medical device of claim 11 wherein the first winding is mounted within an enclosure having a thickness of between approximately 100–1500 microns.

40. An implantable medical device of claim 39 wherein the enclosure of the antenna is approximately 300 microns thick.

41. An implantable medical device of claim 11 wherein the total thickness of the enclosure and windings is no more than approximately 1500 microns.

42. An implantable medical device of claim 11 wherein the thickness of the windings used in the antenna is no more than 100 microns while the canister has a thickness of approximately 0.312 inches.

43. An implantable medical device of claim 11 wherein the ratio of the thickness of the canister to the thickness of the windings used in the antenna is approximately 78.

44. An implantable medical device of claim 11 wherein the thickness of the windings used in the antenna is no more than approximately 1.28% of the thickness of the canister of the device.

45. A method of manufacturing an implantable medical device, comprising:

providing an hermetic canister;

positioning a battery within the hermetic canister;

positioning a pulse generator system within the hermetic canister and electrically coupling the pulse generator to the battery;

positioning a receiver within the hermetic canister and electrically coupling the receiver to the battery and the pulse generator system;

positioning a transmitter within the hermetic canister and electrically coupling the transmitter to the battery and the pulse generator system; and mounting a feedthrough through the hermetic canister such that a first end thereof is disposed within the hermetic canister and is electrically coupled to the transmitter and to the receiver, and such that a second end thereof is disposed outside the hermetic canister providing a planar first antenna mounting the first antenna outside the hermetic canister to the second end of the feedthrough;

wherein the step of providing the first antenna comprises providing a plurality of closely spaced concentric windings of a conductive material therefor, each winding being in the range of approximately 1–100 microns wide and spaced between approximately 1–50 microns apart.

46. The method of manufacturing an implantable medical device of claim 45, further comprising the steps of providing a planar second antenna, coupling the second antenna to the first antenna, and mounting the first antenna outside the hermetic canister to the second end of the feedthrough.

47. A method of manufacturing an implantable medical device, comprising:

providing an hermetic canister;

positioning a battery within the hermetic canister;

positioning a pulse generator system within the hermetic canister and electrically coupling the pulse generator to the battery;

positioning a receiver within the hermetic canister and electrically coupling the receiver to the battery and the pulse generator system;

positioning a transmitter within the hermetic canister and electrically coupling the transmitter in the battery and the pulse generator system; and mounting a feedthrough through the hermetic canister such that a first end thereof is disposed within the hermetic canister and is electrically coupled to the transmitter and to the receiver, and such that a second end thereof is disposed outside the hermetic canister providing a planar first antenna mounting the first antenna outside the hermetic canister to the second end of the feedthrough;

wherein the step of providing the first antenna comprises providing an average surface area of the aperture of the windings used in the first antenna of approximately 0.25 square inches.

48. A method of manufacturing an implantable medical device, comprising:

providing an hermetic canister;

positioning a battery within the hermetic canister;

positioning a pulse generator system within the hermetic canister and electrically coupling the pulse generator to the battery;

positioning a receiver within the hermetic canister and electrically coupling the receiver to the battery and the pulse generator system;

positioning a transmitter within the hermetic canister and electrically coupling the transmitter to the battery and the pulse generator system; and mounting a feedthrough through the hermetic canister such that a first end thereof is disposed within the hermetic canister and is electrically coupled to the transmitter and to the receiver, and such that a second end thereof is disposed outside the hermetic canister providing a planar first antenna mounting the first antenna outside the hermetic canister to the second end of the feedthrough;

wherein the step of providing the first antenna further comprises the steps of:

providing a photo resist material onto a substrate;

placing a mask having apertures over the photo resist material;

transmitting X rays from a device above the mask passes through the apertures to weaken areas of the photo resist bombarded by the X-rays;

removing the weakened areas of the photo resist to create free standing structures of photoresist material;

depositing a material over the free standing photoresist structures;

removing the freestanding photo resist structures;

enclosing the freestanding plated structures within an enclosure; and removing the substrate.

49. The method of manufacturing an implantable medical device of claim 48, further comprising the step of removing excess portions of the material so that the freestanding photo resist structures have a height equal to the material deposited in between.

* * * * *